United States Patent [19]

Kruger et al.

[11] Patent Number: 5,205,821

[45] Date of Patent: Apr. 27, 1993

[54] TERMINAL SELF-RELEASING FLUID RESERVOIR

[75] Inventors: Robert J. Kruger, Arlington Heights; Con A. Lasaitis, Waukegan; Sheldon M. Wecker, Libertyville, all of Ill.

[73] Assignee: Abbott Laboratories, Abbott Park, Ill.

[21] Appl. No.: 786,462

[22] Filed: Nov. 1, 1991

[51] Int. Cl.$^5$ ............................................. A61M 37/00
[52] U.S. Cl. ..................................... 604/91; 604/89; 604/283
[58] Field of Search ............... 604/83, 89, 91, 256, 604/283, 905, 232, 236, 238, 269; 138/89, 91, 96 R, 96 T; 215/2, 211

[56] References Cited

U.S. PATENT DOCUMENTS

| | | | |
|---|---|---|---|
| 2,735,430 | 2/1956 | Huber | 604/238 |
| 3,115,137 | 12/1963 | Sarnoff | 604/238 |
| 3,187,749 | 6/1965 | Sarnoff | 604/238 |
| 3,295,525 | 1/1967 | Evers et al. | 604/232 X |
| 3,811,441 | 5/1974 | Sarnoff | 604/232 X |
| 3,986,645 | 10/1976 | Baldwin et al. | 222/386 |
| 4,432,764 | 2/1984 | Lopez | 604/283 |
| 4,991,629 | 2/1991 | Ernesto et al. | 138/89 |

FOREIGN PATENT DOCUMENTS 0063640  11/1982  European Pat. Off. ............ 604/256

Primary Examiner—C. Fred Rosenbaum
Assistant Examiner—C. Maglione
Attorney, Agent, or Firm—A. Nicholas Trausch; Thomas M. Breininger

[57] ABSTRACT

A terminal reservoir capping device according to the present invention includes a hollow member having first and second open ends. A first plug seals the first open end such that the plug is inwardly displaceable into the hollow member. A second plug seals the second open end. A chamber is defined by the hollow member and the first and second plugs. A reservoir of disinfecting fluid or therapeutic drug is provided in the chamber. Axially extending from the first end of the hollow member is a mechanism for engaging and advancing the tube connector into the chamber so as to inwardly displace the first plug into the chamber. The plug self-releases and allows dispersal of the reservoir fluid into the tube connector.

14 Claims, 2 Drawing Sheets

TERMINAL SELF-RELEASING FLUID RESERVOIR

FIELD OF THE INVENTION

This invention generally pertains to a capping device for connectable tubing used in medical procedures, and more specifically, to a capping device containing a fluid reservoir releasable when joined to a connector in fluid communication with a patient catheter or a fluid administration set, for example.

BACKGROUND OF THE INVENTION

Various medical procedures involve the intermittent administration of drugs or fluids through medical tubing to a patient catheter. This allows the patient to be ambulatory between and/or during the medical procedures. Procedures such as the intermittent infusion of antibiotics often involve an intravenously placed catheter. Procedures such as peritoneal dialysis involve a surgically implanted catheter. These catheters terminate outside the patient's skin with tube connectors mateable to the disposable administration tubing set of the fluid or drug sources.

It is very important to protect and disinfect the reusable connector on the patient catheter before and after the procedure so as to reduce the possibility of infection. For example, it is important to reduce the risk of peritonitis infection in peritoneal dialysis patients since peritoneal membrane injury may lead to premature termination of peritoneal dialysis therapy.

Continuous ambulatory peritoneal dialysis (CAPD) allows a patient to perform peritoneal dialysis during a near normal daily routine. The CAPD patient manually performs 3 to 6 fluid exchanges daily wherever he may be. However, due to the number of exchanges and the variety of environments, CAPD has a high peritonitis rate.

There are currently a number of connector caps in use for sealing and protecting the catheter connection after disconnecting from the dialysis solution administration set. Many of the caps require the user to apply a separately packaged disinfectant to the cap in order to disinfect the connector of the peritoneal catheter. This procedure is time consuming, messy and prone to accidential spills. Often, the disinfection is only partially accomplished which increases the chance of infection.

Other connector caps, such as disclosed in the antibacterial protective cap of Genatempo et al., U.S. Pat. No. 4,440,207 are provided with absorbents containing a disinfectant. However, these absorbents may dry out, may not contain enough disinfectant to provide effective disinfection, or do not deliver the disinfectant to the area of contamination. Also these caps tend to leak when being connected.

A few connector caps contain internal reservoirs of disinfectant that can be engaged with the connector to disinfect the connector while it is not in use. The disadvantage of these known connectors is that they require a great deal of manual dexterity to prepare them for use. Furthermore, they create the potential for accidental spillage and/or leakage because the reservoirs are open prior to connection. For example, the antiseptic end cap of Lopez, U.S. Pat. No. 4,432,764 requires the user to unscrew a cover plug from the end cap prior to use. With the plug removed, the reservoir is open and can be accidently spilled prior to or during connection to the catheter.

The antibacterial closure system of Peluso, U.S. Pat. No. 4,624,664 discloses a capping device whose disinfecting reservoir is exposed once a cover plug is removed. The connector cap and cover of Dadson et al., U.S. Pat. No. 4,938,161 likewise discloses a cap whose reservoir is open and prone to accidental spillage prior to or during connection to the catheter connector.

In general, all of the known capping devices require a high degree of manual dexterity by the patient to prepare and properly connect the connector cap. Also, known devices open the antiseptic or drug reservoir prior to connection to the connector. Accidental spillage prior to connection could decrease the effectiveness of the drug or disinfectant or stain the patient and his clothing.

Thus it is a primary object of this invention to provide a self-contained, disposable, easy to use terminal capping device having a drug or disinfectant reservoir for connectable medical tubing.

It is another object that the drug or disinfectant in the capping device be self-releasing so as to minimize accidental spilling or leakage, especially before connections.

It is another object that the device allow the contained disinfectant to cover the outside rim and engaging parts of the connector and diffuse throughout the internal pathway of the connector.

A terminal capping device according to the present invention includes a hollow cylindrical body member having first and second open ends. A first plug seals the first open end such that the plug is inwardly displaceable into the cylindrical body member. A second plug seals the second open end. A chamber is defined by the cylindrical body member and the first and second plugs. A reservoir of disinfecting fluid or drug is provided in the chamber. Axially extending from the first end of the cylindrical body member is a mechanism for engaging and advancing the tube connector into the chamber so as to inwardly displace the first plug into the chamber. This allows dispersal of the reservoir fluid into the tube connector.

DETAILED DESCRIPTION OF THE DRAWINGS

Figure 1:
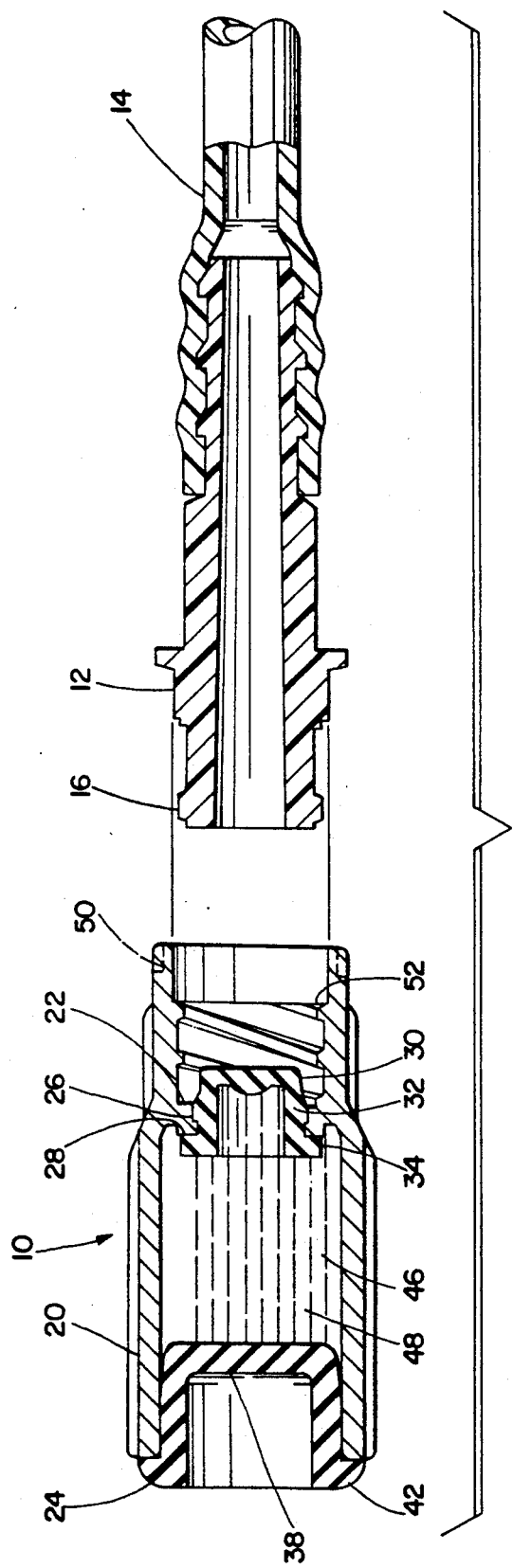
FIG. 1 is a sectional view of the terminal capping device of the present invention and a tube connector prior to engagement.

Referring now to FIG. 1, the terminal capping device 10 of the present invention is shown with a connectable tube connector 12 in fluid communication with a patient catheter, for example. The connector 12 may also be the distal end of an administration set. The specific connector shown in FIG. 1 is a male luer adapter and has external threads 16, but the present invention is applicable to any type of connectable medical tubing.

The capping device 10 includes a hollow body 20, preferably semi-rigid and cylindrical, having a first open end 22 and a second open end 24. The first open end has a radially inward extending annular flange 26 extending from the cylindrical body so as to create an orifice 28. The diameter of the orifice is smaller than the inner diameter of the cylindrical body 10.

A first plug 30 includes a plug portion 32 and a radial flange portion 34. The plug 30 is made of a suitable medical material more resilient than the material of the hollow body 20. The plug portion 32 includes an integral seal ring 35 and is of proper diameter to sealingly engage by a friction fit in the orifice 28. The flange portion 34 abuts the face of the circumferential flange 26 on the inside (i.e., chamber side) of the hollow body. The first plug is sealingly engaged in the orifice 28 with the plug flange 34 abutting the inside or inward face of the body flange 26. Thus the plug 30 is inserted into position from the open second end 24 of the hollow body. The outer diameter of the plug flange 34 is smaller than the inner diameter of the hollow body 20 to allow the plug to be inserted through the hollow body. The indented portion 37 of the plug facilitates a fixture being used to sealingly seat the plug 30 in the orifice 28.

The second open end 24 of the hollow body can be closed by any closure member that is sealable across the open end. For example, a flat disc can be circumferentially fixed onto the end of the hollow body.

Alternatively, a second plug 38 can be used. The second plug 38 is of larger diameter than the first plug and includes a plug portion 40 and a flange portion 42. The plug portion 42 is of proper diameter to engage in the second open end of the hollow cylindrical body. The flange portion 42 abuts the circumferential edge of the cylindrical body. The second plug is fixed in place by adhesive bonding or ultrasonic welding or other suitable bonding techniques to prevent removal.

The cylindrical body 20 and the two end plugs 30 and 40 when sealingly in place form a sealed, enclosed chamber 46. After the first plug 30 is sealingly engaged in the orifice 28, but before the second plug 40 is permanently sealed to the cylindrical body 20, the chamber 46 is only partially filled with a medical substance 48 so as to allow the first plug to be displaced into the chamber.

The first end of the cylindrical body 20 includes an axial extension 50. The extension includes any of a known variety of engaging and advancing constructions such as, for example, threaded fitments or luer connections.

In the embodiment of FIG. 1, the axial extension is a female luer adapter and includes internal threads 52 adapted to mate with the external threads 16 of the male luer connector 12. The internal threads 52 engage and advance the tube connector 12 towards the chamber 46.

Figure 2:
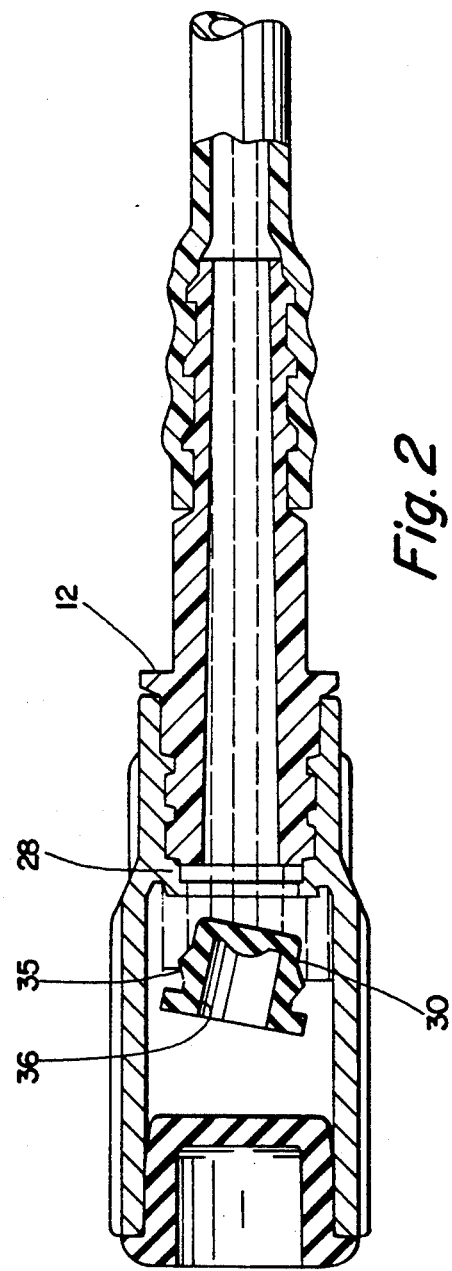
FIG. 2 is a sectional view of the capping device and tube connector of FIG. 1 after engagement.

As shown in FIG. 2, as the patient merely screws the cap 10 onto the connector 12, the tube connector advances into contact with the first plug 30 and displaces the plug into the part-filled chamber 46. The reservoir fluid 46 can now diffuse into and around the connector 12.

Figure 3:
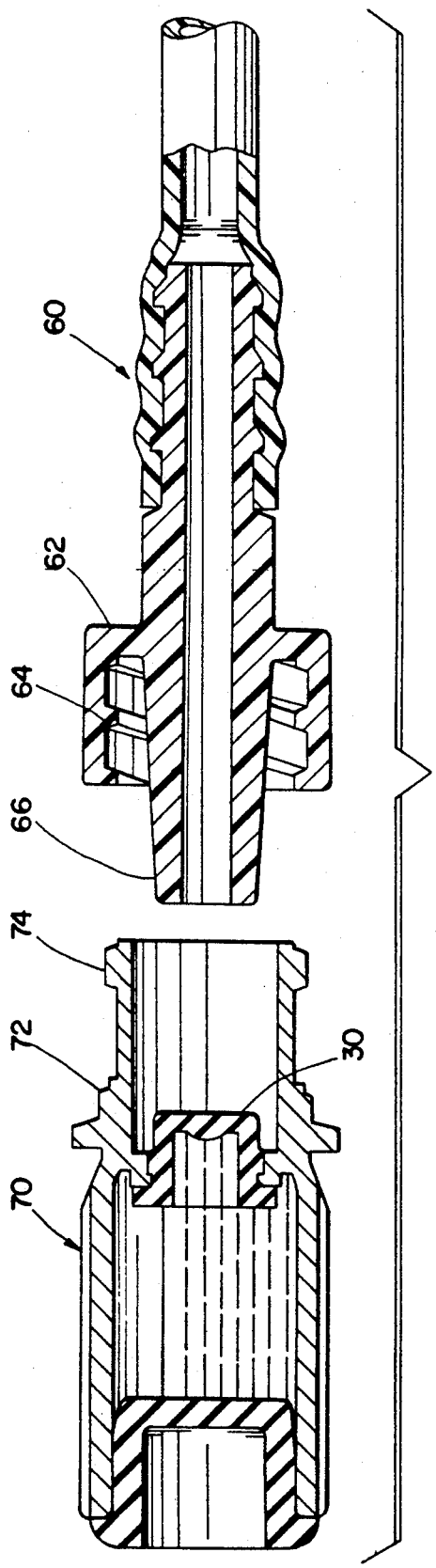
FIG. 3 is a sectional view of an alternate embodiment of a capping device for use for with alternate embodiment of a tube connector, prior to engagement.
Figure 4:
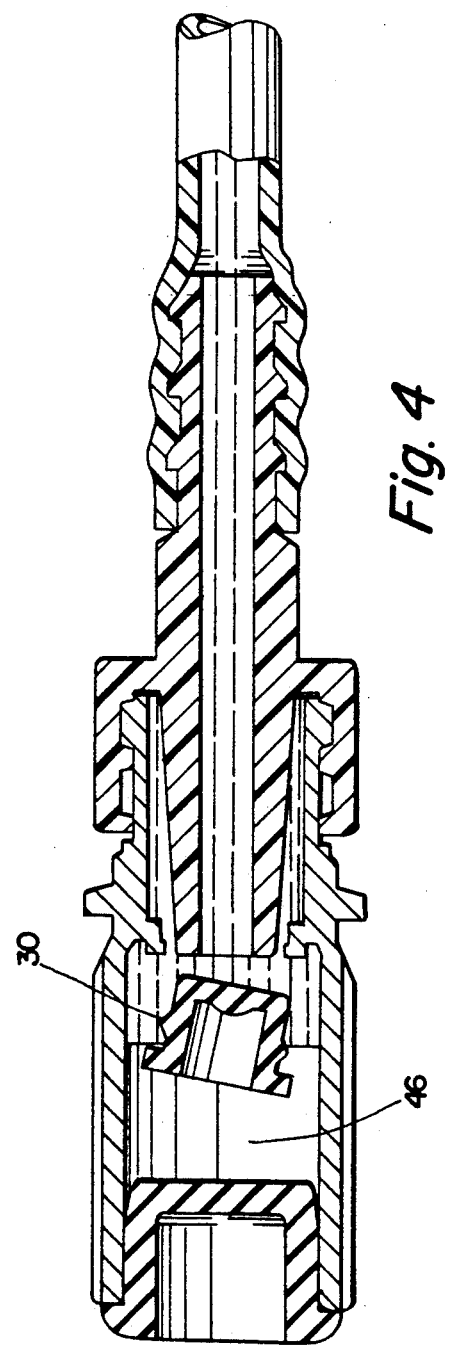
FIG. 4 is a sectional view of the capping device and tube connector of FIG. 3 after engagement.

An alternate embodiment of the connector and capping device is shown in FIGS. 3 and 4. The connector 60 of FIG. 3 includes a skirt 62 having internal threads 64. An axial flow projection 66 provides flow communication to the tube 14.

The capping device 70 is constructed similar to the previously described capping device 10, except that the axial extension 72 has external threads 74 which engage and mate with internal threads 64 of the connector. As the threads are advanced on each other, the flow passage axial projection 66 contacts the first plug 30. Upon further advancement, the axial projection pushes the plug 30 into the chamber 46 and causes the reservoir fluid to disperse into and around the end of the connector 60.

When used as a capping device for a peritoneal dialysis connector, the medical substance 48 would be a disinfectant fluid, preferably povidone-iodine. Other suitable disinfectants include chlorhexidine. The volume of the chamber 46 for a terminal peritoneal dialysis capping device is on the order of 1.0 ml and is approximately 60% filled with either a fluid or a powder.

It is envisioned that the capping device 10 or 70 could also be used as a reservoir for other medical solutions, such as heparin or saline to flush the catheter at the end of an infusion procedure. It is also envisioned within the scope of this invention to modify the capacity of the chamber 46 and include therein antiseptic and therapeutic drugs such as liquid or powder antibiotics for quick and safe connection for infusion to an implanted catheter. Furthermore, a diagnostic fluid could easily be introduced into the fluid flow. Thus, a terminal reservoir device with the self-releasing plug would facilitate intermittent administration of the various medical substances quickly and safely.

Alternatively, the enclosed chamber 46 could be initially sealed empty. This would allow the terminal reservoir to be used to safely collect a sample of the fluid in the medical tubing for further diagnostic purposes.

All of the embodiments described above are constructed of suitable medical class materials so as to be compatible with the fluids and medical substance contained in the capping device and flowing in the tubing.

Furthermore, the capping device of the present invention can be readily sterilized after filling and final sealing at the second end by traditional methods such as radiation or autoclaving. For some uses, such as a disinfectant reservoir for CAPD use, the capping device does not necessarily have to be sterilized.

The foregoing invention can be practiced by those skilled in the art. Such skilled persons will appreciate that the terminal reservoir device of the present invention is not necessarily restricted to the particular preferred embodiments presented herein. The scope of the invention is to be defined by the terms of the following claims in the spirit and meaning of the preceding description.

We claim:

1. A terminal reservoir device for a connectable tube connector, comprising:
   a hollow member having first and second open ends;
   first means for sealing said first open end, said first sealing means being inwardly displaceable into the hollow member;
   second means for sealing said second open end;
   an enclosed chamber defined by said hollow member, said first sealing means and second sealing means; and
   means axially extending from said first end of said hollow member for engaging and advancing the connectable tube connector toward said chamber so as to inwardly displace the first sealing means into said chamber, wherein said first sealing means is a first plug member sealingly engageable in the first open end of the hollow member from the direction of the second end only.

2. The terminal reservoir device of claim 1 further including a medical substance contained in said enclosed chamber.

3. The terminal reservoir device of claim 2 wherein said first open end includes a radially inward extending annular flange defining an orifice and wherein said first plug member includes a plug portion and a flange portion, said plug portion having a sealing friction fit in said orifice and said flange portion abutting said annular flange.

4. The terminal reservoir device of claim 3 wherein said second sealing means is a member adapted to sealingly close the second open end after the medical substance is positioned in said hollow member.

5. The terminal reservoir device of claim 4 wherein said closing member is a second plug member including a second plug portion sealingly engageable in the hollow member and a second flange portion abutting said second open end.

6. The terminal reservoir device of claim 5 wherein said flange portion of said first plug has a smaller diameter than said hollow member so that said first plug is sealingly engaged in said orifice and said chamber is partially filled with said medical substance before said second plug is sealingly engaged in said second open end.

7. The terminal reservoir device of claim 6 wherein said engaging and advancing means includes an internally threaded axial extension.

8. The terminal reservoir device of claim 6 wherein said engaging and advancing means includes an externally threaded axial extension.

9. The terminal reservoir device of claim 6 wherein said medical substance is a disinfectant.

10. The terminal reservoir device of claim 9 wherein said disinfectant is povidone iodine.

11. The terminal reservoir device of claim 2 wherein said medical substance is a disinfectant.

12. The terminal reservoir device of claim 2 wherein said medical substance is a therapeutic drug.

13. The terminal reservoir device of claim 2 wherein said medical substance is a dignostic fluid.

14. The terminal reservoir device of claim 1 wherein said chamber is an empty reservoir suitable for collecting a fluid sample.

* * * * *